(12) United States Patent
Tamura et al.

(10) Patent No.: US 10,624,534 B2
(45) Date of Patent: Apr. 21, 2020

(54) LIGHT SOURCE DEVICE

(71) Applicant: OLYMPUS CORPORATION, Tokyo (JP)

(72) Inventors: Kazuaki Tamura, Hachioji (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 364 days.

(21) Appl. No.: 15/630,473

(22) Filed: Jun. 22, 2017

(65) Prior Publication Data

US 2017/0290498 A1 Oct. 12, 2017

Related U.S. Application Data

(63) Continuation of application No. PCT/JP2014/084360, filed on Dec. 25, 2014.

(51) Int. Cl.
*F21V 9/30* (2018.01)
*F21V 7/00* (2006.01)
(Continued)

(52) U.S. Cl.
CPC ........ *A61B 1/0653* (2013.01); *A61B 1/00006* (2013.01); *A61B 1/00096* (2013.01); *A61B 1/0638* (2013.01); *A61B 1/0676* (2013.01); *A61B 1/07* (2013.01); *F21V 7/00* (2013.01); *F21V 9/30* (2018.02); *F21V 14/00* (2013.01); *G02B 6/0008* (2013.01);
(Continued)

(58) Field of Classification Search
CPC ............. F21V 33/0068; F21V 2200/10; F21V 2200/30; F21V 23/06

USPC .................................................. 362/551–582
See application file for complete search history.

(56) References Cited

U.S. PATENT DOCUMENTS

2008/0267562 A1* 10/2008 Wang ................... A61B 5/0062
362/572
2014/0022810 A1* 1/2014 Ito ....................... G01N 21/8806
362/551

FOREIGN PATENT DOCUMENTS

JP H05-323211 A 12/1993
JP H10-239740 A 9/1998
(Continued)

OTHER PUBLICATIONS

Japanese Office Action dated Jun. 26, 2018 in Japanese Patent Application No. 2016-565768.
(Continued)

*Primary Examiner* — William J Carter
(74) *Attorney, Agent, or Firm* — Scully, Scott, Murphy & Presser, P.C.

(57) ABSTRACT

A light source device includes a primary light source that emits primary light, a light guide that guides the primary light, an optical conversion unit that converts the primary light emitted from the light guide and having a first light distribution angle into secondary light having a second light distribution angle and emits the secondary light, and a light distribution adjustment unit that adjusts the secondary light to illumination light having a third light distribution angle and emits the illumination light. The light distribution adjustment unit and the optical conversion unit slide each other. The light distribution adjustment unit allows a light distribution adjustment amount for adjusting the second light distribution angle of the secondary light to adjust to the third light distribution angle of the illumination light.

13 Claims, 7 Drawing Sheets

(51) Int. Cl.
*A61B 1/06* (2006.01)
*G02B 23/24* (2006.01)
*A61B 1/00* (2006.01)
*A61B 1/07* (2006.01)
*F21V 14/00* (2018.01)
*F21V 8/00* (2006.01)
*F21Y 115/30* (2016.01)
*F21V 3/02* (2006.01)

(52) U.S. Cl.
CPC ..... *G02B 23/2461* (2013.01); *G02B 23/2469* (2013.01); *F21V 3/02* (2013.01); *F21Y 2115/30* (2016.08)

(56) References Cited

FOREIGN PATENT DOCUMENTS

| | | |
|---|---|---|
| JP | 2012-135432 A | 7/2012 |
| JP | 2013-000175 A | 1/2013 |
| JP | 2013-198547 A | 10/2013 |
| JP | 2013-244297 A | 12/2013 |
| JP | 2014-023815 A | 2/2014 |
| JP | 2014-124490 A | 7/2014 |

OTHER PUBLICATIONS

International Search Report dated Mar. 24, 2015 issued in PCT/JP2014/084360.

English translation of International Preliminary Report on Patentability dated Jul. 6, 2017 together with the Written Opinion received in related International Application No. PCT/JP2014/084360.

\* cited by examiner

LIGHT SOURCE DEVICE

CROSS-REFERENCE TO RELATED APPLICATIONS

This application is a Continuation application of PCT Application No. PCT/JP2014/084360, filed Dec. 25, 2014, the entire contents of all of which are incorporated herein by references.

BACKGROUND OF THE INVENTION

1. Field of the Invention

The present invention relates to a light source device that converts primary light emitted from a light source into secondary light having different optical characteristics and emits the light.

2. Description of the Related Art

A light source device has been developed that converts optical characteristics of light emitted from a small solid light source by an optical converter and emits the light as illumination light. For example, Jpn. Pat. Appln. KOKAI Publication No. 2013-244297 discloses a light source device that allows illumination light of desired irradiation patterns and colors using an adapter detachable to the light source device. The light source device includes an optical conversion unit that converts excitation light emitted via a light guide from a light source by an optical converter and emits light as illumination light. To the light source device, an adapter having an incident diameter larger than a diameter of an emission unit of the optical conversion unit is attached. This light source device enables light emitted from the optical conversion unit to guide to the adapter and to change optical characteristics of the illumination light.

BRIEF SUMMARY OF THE INVENTION

A light source device of an embodiment in the present invention comprises a primary light source that emits primary light, a light guide that guides the primary light, an optical conversion unit that converts the primary light emitted from the light guide and having a first light distribution angle into secondary light having a second light distribution angle different from the first light distribution angle and emits the secondary light, and a light distribution adjustment unit that adjusts the secondary light having the second light distribution angle to illumination light having a third light distribution angle and emits the illumination light. One of the light distribution adjustment unit and the optical conversion unit is arranged to be slidable to the other. The light distribution adjustment unit is configured to adjust a light distribution adjustment amount that is an amount for adjusting the second light distribution angle of the secondary light to the third light distribution angle of the illumination light.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

DETAILED DESCRIPTION

First Embodiment (Configuration)

Figure 1:
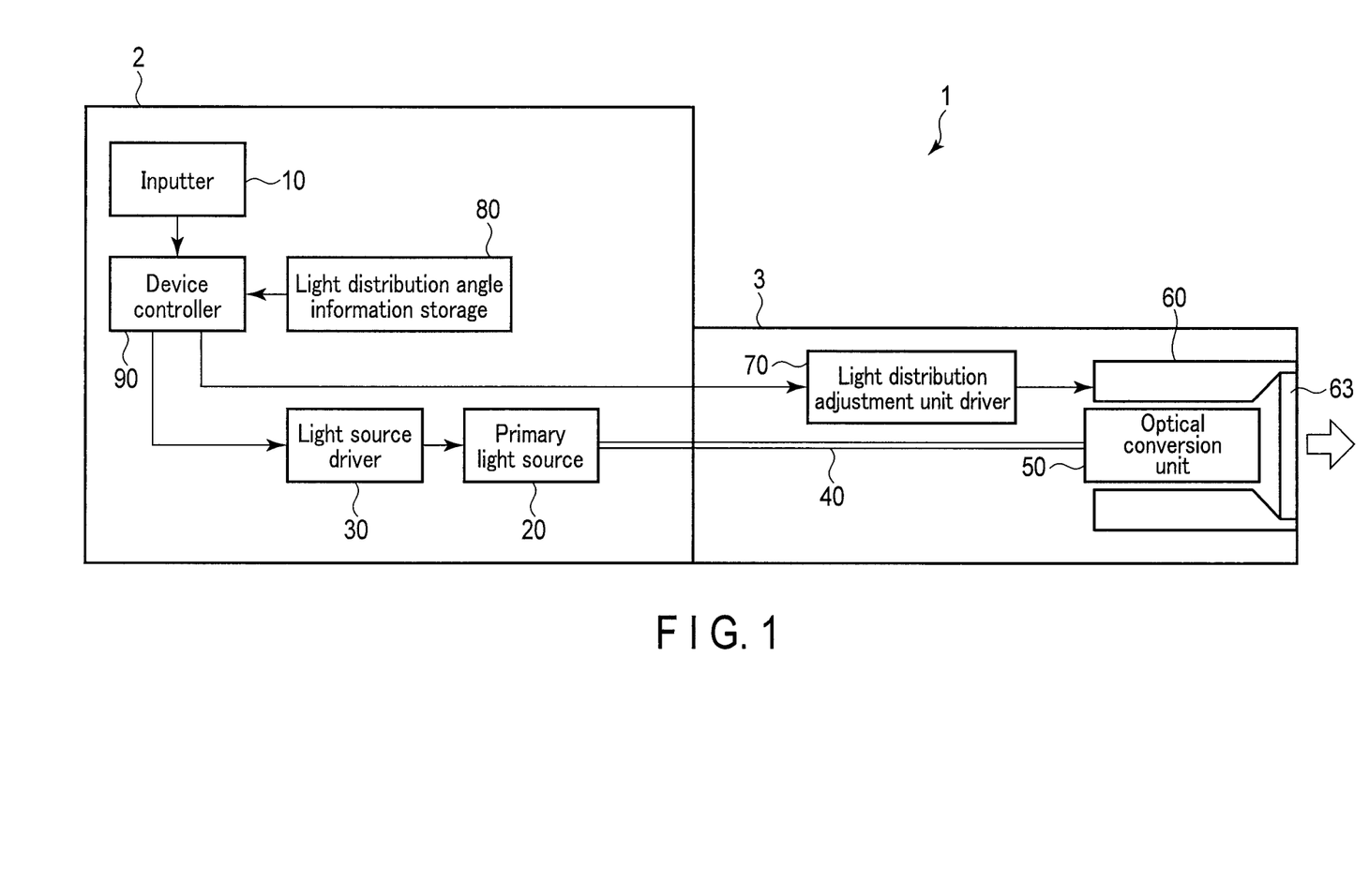
FIG. 1 is a block diagram schematically showing a light source device according to a first embodiment.

FIG. 1 is a block diagram schematically showing a light source device 1 according to the first embodiment. The light source device 1 comprises an inputter (input unit) 10, a laser diode (LD) 20 which is a primary light source, a light source driver 30, an optical fiber 40, an optical conversion unit 50, a light distribution adjustment unit 60, a light distribution adjustment unit driver 70, a light distribution angle information storage 80, and an device controller 90. The inputter 10, the LD 20, the light source driver 30, the light distribution angle information storage 80, and the device controller 90 are arranged in a main body 2 of the light source device 1. The optical conversion unit 50, the light distribution adjustment unit 60, and the light distribution adjustment unit driver 70 are arranged in an elongated insertion section 3 coupled to the main body 2. The optical fiber 40 extends from the LD 20 of the main body 2 to the optical conversion unit 50 of the insertion section 3.

In the present embodiment, it is assumed that the insertion section 3 is inserted into an insertion target to apply illumination light to the insertion target; thus, what is represented by reference number 3 is referred to as an "insertion section". However, the insertion section 3 is not limited to use for insertion into the insertion target and may be used without being inserted.

(Inputter)

The inputter 10 includes general input devices such as a switch, a keyboard, etc. The inputter 10 further includes a user interface having functions of operating a power source of the light source device 1 (ON/OFF), setting light amount adjustment of the illumination light emitted from the light source device 1, and adjustment of light distribution angles of the illumination light. In the inputter 10, a user enters, for example, a mode selected from a wide light distribution mode, a first narrow light distribution mode and a second narrow light distribution mode, which will be described later.

(Primary Light Source)

The primary light source in the present embodiment is the laser diode (LD) 20 that emits blue laser light having a light emitting wavelength peak of 445 nm. Thus, primary light in the present embodiment is defined as blue laser light having a peak at a wavelength of 445 nm.

(Light Source Driver)

To drive the LD 20 of the primary light source, the light source driver 30 supplies to the LD 20 a required power that depends upon a predetermined driving current and driving intervals based upon a control signal from the device controller 90.

(Optical Fiber)

The optical fiber 40 is a light guide having flexibility in which the proximal end (incident end) and the distal end (emission end) 41 of the optical fiber 40 are optically coupled to the LD 20 and the optical conversion unit 50, respectively. The optical fiber 40 guides the blue laser light emitted from the LD 20 to the optical conversion unit 50. The optical fiber 40 in the present embodiment is, for example, a multimode optical fiber having a core diameter of 50 μm and numerical aperture FNA=0.2.

(Optical Conversion Unit)

The optical conversion unit 50 is arranged near the distal end of the insertion section 3 and fixed inside the insertion section 3 by an adhesive member, etc. The optical conversion unit 50 receives the primary light guided through the optical fiber 40 and emitted from the emission end 41 thereof, converts the primary light into secondary light having light distribution characteristics different from those of the primary light, and emits the light. The light distribution characteristics of the secondary light emitted from the optical conversion unit 50 has properties that do not change due to the amount of the entering primary light.

Figure 2:
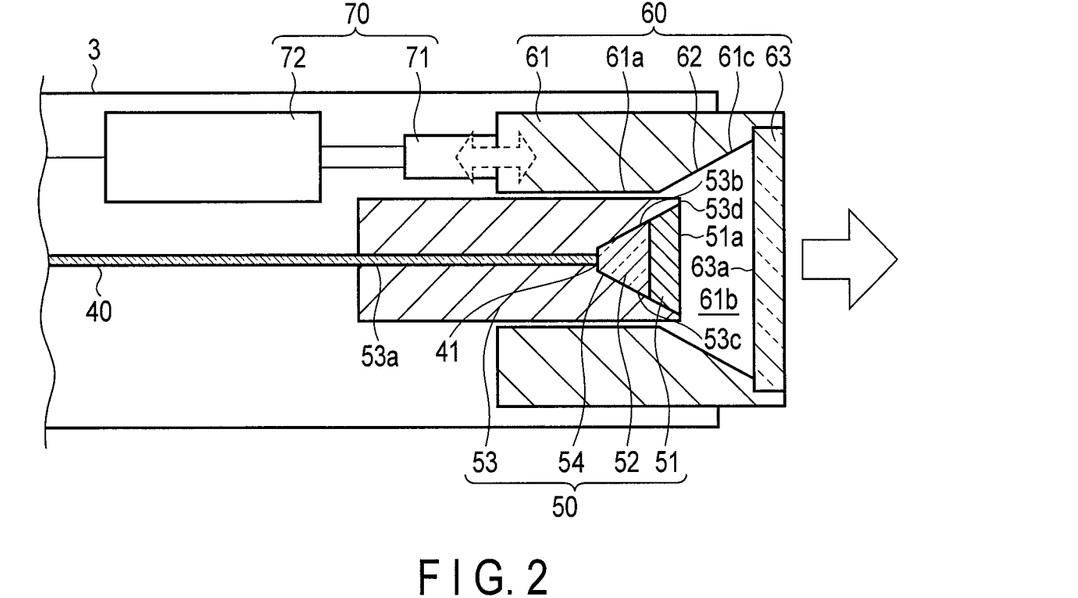
FIG. 2 is a view schematically showing a distal end of the light source device according to the first embodiment.

FIG. 2 is a view schematically showing a distal end of the light source device 1 in the first embodiment. The optical conversion unit 50 includes an optical converter 51, a transparent member 52, a first holder 53, and a first reflector 54.

The optical converter 51 includes a phosphor and a diffuser functioning as wavelength converters. The optical converter 51 further includes a sealant that seals the phosphor and the diffuser. The phosphor in the present embodiment has properties of absorbing the primary light (blue laser light) emitted from the LD 20 and performing wavelength conversion to provide light having a wavelength longer than that of the primary light. Specifically, the phosphor includes a phosphor powder represented by YAG:Ce, and the phosphor absorbs light of a blue wavelength band and performs wavelength conversion to provide yellow fluorescence. The diffuser in the present embodiment expands a spread angle of the primary light that has entered the light diffuser without changing its wavelength and converts the light into the diffused light having weakened coherence. Specifically, the diffuser is formed by dispersing diffusion particles of alumina having a higher refractive index than that of a sealing material into the transparent sealing material such as a silicone resin and hardening the silicon resin. When the optical converter 51 is obtained by combining the particles of alumina having the refractive index of 1.7 or more and the silicon resin having the refractive index of 1.4 or more, if the optical converter 51 whose volume concentration of 20% and the thickness of 0.1 mm or so is used, it allows the diffused light of the primary light emitted from the optical fiber emission end 41 to be sufficiently increased and the light distribution angle of the primary light emitted from the optical conversion unit 50 to be sufficiently expanded.

The transparent member 52 is made of glass or a silicone resin having a high transmittance. The transparent member 52 has properties of transmitting the primary light emitted from the optical fiber emission end 41 and the wavelength conversion light radiated from the optical converter 51.

The first holder 53 holds the optical fiber 40 (optical fiber emission end 41), the optical converter 51, and the transparent member 52. The first holder 53 is, for example, a cylindrical member extending in the longitudinal direction of the insertion section 3. The first holder 53 includes a fiber holding hole 53a at the proximal side, and a truncated-conical shaped hollow portion 53b at the distal side connected to the fiber holding hole 53a. The fiber holding hole 53a has an inner diameter approximately the same as the outer diameter of the optical fiber 40, and the optical fiber emission end 41 is inserted and held in the fiber holding hole 53a. The hollow portion 53b is expanded along the emission direction of the primary light from the optical fiber emission end 41. That is, the hollow portion 53b is a portion that is open to expand toward the distal end of the first holder 53, and is defined by a first taper surface 53c in the first holder 53.

In the hollow portion 53b of the first holder 53, the transparent member 52 and the optical converter 51 are arranged in this order while being in contact with each other in the emission direction of the primary light from the optical fiber emission end 41. The emission surface 51a of the optical converter 51 and the tip surface 53d of the first holder 53 are arranged on approximately the same plane.

A taper angle of the first taper surface 53c preferably falls within the range of 10 to 60° to efficiently take out from the optical conversion unit 50 omnidirectional fluorescent components and the primary light diffused by the diffuser. The taper angle of the first taper surface 53c in the present embodiment is 25°.

The first reflector 54 is formed on the first taper surface 53c of the first holder 53. The first reflector 54 in the present embodiment is a metal reflection film formed by thinly plating the first taper surface 53c with a metal such as silver or aluminum. When the primary light, and the light (fluorescence) that has been wavelength converted by the optical converter 51 enters the first reflector 54, the first reflector 54 performs specular reflection or diffuse reflection of the light that has entered.

(Light Distribution Adjustment Unit)

The light distribution adjustment unit 60 receives the secondary light emitted from the optical conversion unit 50 and having fixed light distribution characteristics and changes the light distribution characteristics of the received secondary light, thereby allowing emission as illumination light. The light distribution adjustment unit 60 is coupled to the light distribution adjustment unit driver 70 and configured to be movable in the optical axis direction of the primary light emitted from the optical fiber emission end 41*a*. The light distribution adjustment unit 60 changes light distribution characteristics of the secondary light emitted from the optical conversion unit 50 in accordance with a relative position (distance) in the optical axis direction between the emission surface 51*a* of the optical conversion unit 50 and a coverglass incident surface 63*a*, which will be described later, of the light distribution adjustment unit 60. In other words, the light distribution adjustment unit 60 has properties in that the light distribution characteristics adjustment amount varies depending on the relative position between the emission surface 51*a* and the coverglass incident surface 63*a*.

The light distribution adjustment unit 60 in the present embodiment includes a second holder 61, a second reflector 62, and a coverglass 63.

The second holder 61 includes a through hole formed of a guide hole 61*a* at the proximal side, and a truncated-conical shaped hollow portion 61*b* at the distal side connected to the guide hole 61*a*. The guide hole 61*a* includes an inner diameter larger than an outer diameter of the first holder 53, and the first holder 53 is arranged inside the guide hole 61*a*. The hollow portion 61*b* is expanded along the emission direction of the secondary light from the emission surface 51*a* of the optical conversion unit 50. That is, the hollow portion 61*b* is a portion that is open to expand toward the distal end of the second holder 61 and is defined by the second taper surface 61*c* inside the second holder 61. At the proximal end of the second holder 61, a screw hole (not shown) is formed where a ball screw 71, which will be described later, of the light distribution adjustment unit driver 70 is screwed.

The second reflector 62 is formed on the second taper surface 61*c* of the second holder 61. The second reflector 62 is arranged at a portion excluding a region on the optical axis of the primary light emitted from the optical fiber emission end 41. The second reflector 62 in the present embodiment is a metal reflection film formed by thinly plating the first taper surface 61*c* with a metal such as silver or aluminum. The second reflector 62 performs specular reflection or diffuse reflection with respect to the light that has entered when the secondary light (primary diffused light and fluorescence) enters. That is, the second reflector 62 receives the secondary light and changes a traveling direction of the secondary light.

The coverglass 63 is an optical transmission member for emitting, as illumination light, the secondary light whose light distribution characteristics have been changed. The coverglass 63 is, for example, made of glass having a high light transmittance. The coverglass 63 is, for example, formed into a disk shape and adhered and fixed to the emission end side of the second holder 61. In the present embodiment, the coverglass incident surface 63*a* and the emission surface 51*a* of the optical converter 51 of the optical conversion unit 50 are substantially orthogonal to the optical axis of the primary light emitted from the optical fiber emission end 41 and arranged substantially in parallel.

(Light Distribution Adjustment Unit Driver)

The light distribution adjustment unit driver 70 moves (advances and retreats) the light distribution adjustment unit 60 forward and backward on the optical axis of the primary light emitted from the optical fiber emission end 41. Upon receipt of the driving signal from the device controller 90, the light distribution adjustment unit driver 70 is driven to slide the light distribution adjustment unit 60 on the optical axis of the primary light. The light distribution adjustment unit driver 70 includes, for example, the ball screw 71 that is a holder and a micromotor 72 coupled to the ball screw 71.

The ball screw 71 is screwed to the screw hole (not shown) formed on the second holder 61 of the light distribution adjustment unit 60. When the ball screw 71 is rotationally driven in one direction by the micromotor 72, the light distribution adjustment unit 60 moves in the traveling direction on the optical axis with respect to the optical conversion unit 50, and when the ball screw 71 is driven in the other direction, the light distribution adjustment unit 60 moves in a direction opposite to the traveling direction on the optical axis.

In the present embodiment, the light distribution adjustment unit 60 is arranged to be slidable with respect to the optical conversion unit 50 by the light distribution adjustment unit driver 70.

(Light Distribution Angle Information Storage)

The light distribution angle information storage 80 stores light distribution characteristics control information in which a relative position (distance) between the emission surface 51*a* of the optical converter 51 of the optical conversion unit 50 and the coverglass incident surface 63*a* of the light distribution adjustment unit 60 is associated with light distribution characteristics (light distribution angle) of illumination light. The light distribution characteristics control information includes light distribution angle information when the relative position (distance) between the optical conversion unit 50 and the light distribution adjustment unit 60 changes in a stepwise or continuous manner (see FIG. 9). The light distribution angle information storage 80 further stores light distribution angle information (fixed value) of the secondary light emitted from the optical conversion unit 50. These items are information obtained by measurement performed in advance at the time of manufacturing the light source device 1 and shipping, for example. The information stored in the light distribution angle information storage 80 is read out by the device controller 90.

Figure 9:
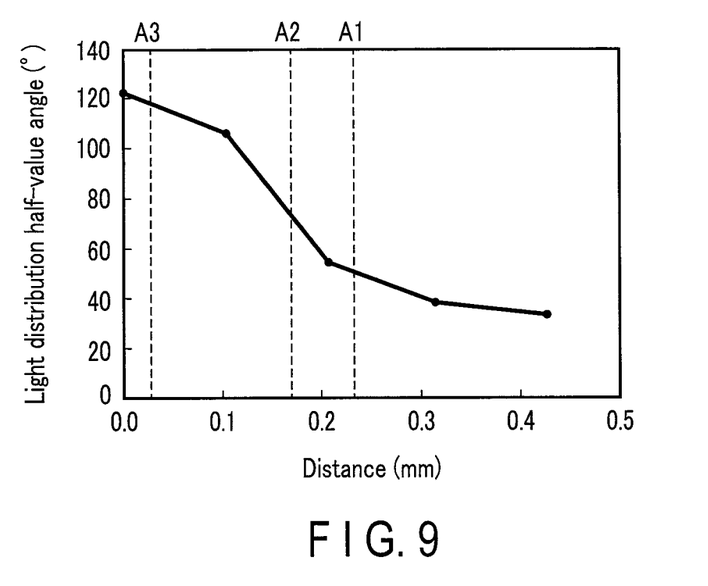
FIG. 9 is a diagram showing an example of a relationship between a distance of an emission surface of an optical conversion unit and a coverglass incident surface of a light distribution adjustment unit, and a light distribution half-value angle of the illumination light.

The light distribution angle information storage 80 is not limited to a main storage provided in the main body 2 and may be an external storage separate from the main body 2 such as an optical disc and a flash memory storing the above-mentioned light distribution characteristics control information, etc. Furthermore, the light distribution characteristics control information is not limited to continuous information as illustrated in FIG. 9 and may be information in a form of a stepwise (discrete) table.

(Apparatus Controller)

The device controller 90 is communicatively connected to the light source driver 30 and the light distribution adjustment unit driver 70. The device controller 90 transmits the control signal to the light source driver 30 to drive the LD 20.

Furthermore, in order to realize an operation condition of the light source device 1 input from the inputter 10 (e.g., a wide light distribution mode, a first narrow light distribution mode or a second narrow light distribution mode, which will be described later), the device controller 90 transmits the control signal to the light distribution adjustment unit driver 70, and the light distribution adjustment unit driver 70 adjusts light distribution by the light distribution adjustment unit 60. In particular, the device controller 90 has a function of reading out, from the light distribution angle information storage 80, the light distribution characteristics control information that is stored in the light distribution angle information storage 80. The light distribution characteristics information indicates the relation between the light distribution angle of illumination light and the positional relationship between the light distribution adjustment unit 60 and the optical conversion unit 50. The device controller 90 also has functions of calculating a moving amount of the light distribution adjustment unit 60 required to obtain illumination light having desired light distribution characteristics, and controlling the micromotor 72 of the light distribution adjustment unit driver 70 based on the moving amount. The device controller 90 further includes functions of extracting a control amount (rotation driving amount) by the micromotor of the light distribution adjustment unit driver 70 and the positional relation between the light distribution adjustment unit 60 and the optical conversion unit 50.

Moreover, the device controller 90 has a function of controlling the light distribution adjustment unit driver 70 in synchronization with a driving timing of driving the LD 20 by the light source driver 30. For switching the light distribution characteristics of the illumination light, the device controller 90 has a function of switching the light distribution adjustment unit driver 70 by not only manual input from the inputter 10 but, for example, automatic switching based on an irradiation pattern, etc. of a predetermined light distribution angle that is set in advance.

(Operation)

The user enters into the inputter 10 a mode selected from three operation modes of the light source device 1, i.e., a wide light distribution mode, a first narrow light distribution mode and a second narrow light distribution mode. Information on the entered mode is transmitted from the inputter 10 to the device controller 90. The device controller 90 reads out the light distribution characteristics control information corresponding to the selected mode from the light distribution angle information storage 80 and controls the light distribution adjustment unit driver 70 to change the relative position of the light distribution adjustment unit 60 to the optical conversion unit 50. For example, the device controller 90 controls the position of the light distribution adjustment unit 60 with respect to the optical conversion unit 50 in a stepwise manner by the light distribution adjustment unit driver 70.

Hereinafter, descriptions will be given on the operation of the light source device 1 in each mode, and the illumination light emitted from the light source device 1 in each mode.

(Operation in Wide Light Distribution Mode)

Figure 3:
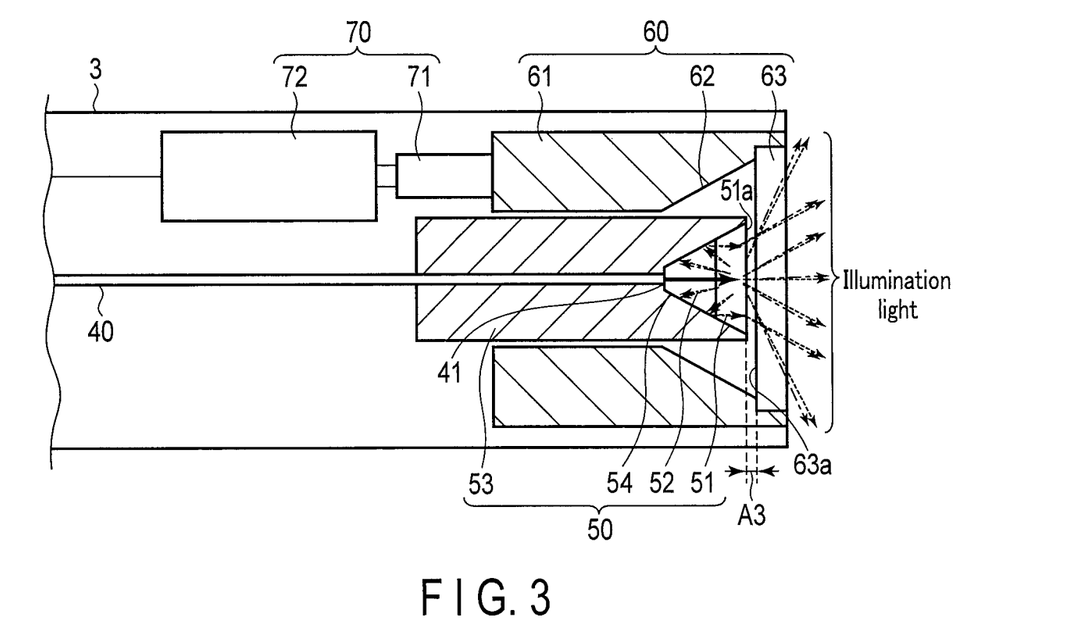
FIG. 3 is a view showing an example of primary light, primary diffused light, and fluorescence when illumination light is emitted from the light source device in a wide light distribution mode.
Figure 4:
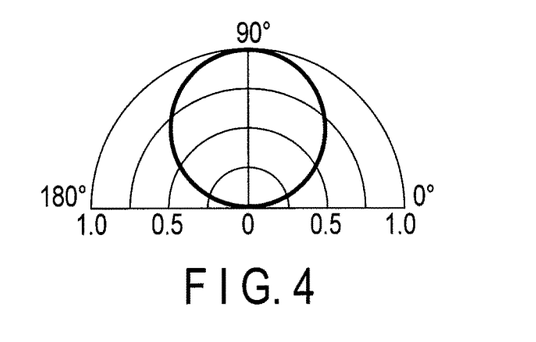
FIG. 4 shows an example of light distribution characteristics of illumination light in the wide light distribution mode.

FIG. 3 is a view showing an example of primary light, primary diffused light, and fluorescence when illumination light is emitted from the light source device 1 in a wide light distribution mode. FIG. 4 is a view showing an example of light distribution characteristics of illumination light in the wide light distribution mode.

The wide light distribution mode is a mode in which the light source device 1 emits illumination light having a wide light distribution (e.g., light distribution half-value angle of 120°). When the user selects the wide light distribution mode, the device controller 90 reads out, from the light distribution characteristics control information stored in the light distribution angle information storage 80, distance A3 (FIGS. 3 and 9) corresponding to the light distribution angle between the emission surface 51a of the optical conversion unit 50 and the coverglass incident surface 63a of the light distribution adjustment unit 60. The device controller 90 drives the light distribution adjustment unit driver 70 to move the light distribution adjustment unit 60 in the optical axis direction so that the distance between the emission surface 51a and the coverglass incident surface 63a becomes A3.

For example, the device controller 90 obtains the current positional information of the coverglass incident surface 63a with respect to the emission surface 51a of the optical conversion unit 50 before or immediately after information on the input mode is obtained, or immediately after distance A3 is read out from the light distribution angle information storage 80. The device controller 90 calculates the moving amount of the light distribution adjustment unit 60 from the obtained current locational information and the distance A3 after distance A3 is read out from the light distribution angle information storage 80 and before the light distribution adjustment unit driver 70 is driven. Based on the calculated moving amount, the device controller 90 transmits the driving signal to the light distribution adjustment unit driver 70 to drive the light distribution adjustment unit driver 70, and moves the light distribution adjustment unit 60 to a desired position in the optical axis direction.

After completion of moving, the device controller 90 transmits the control signal to the light source driver 30. The light source driver 30 transmits the driving signal to the LD 20 to drive the LD 20.

Alternatively, during a drive control period when the LD 20 is being driven by the light source driver 30, the device controller 90 transmits the driving signal to the light distribution adjustment unit driver 70 to drive the light distribution adjustment unit driver 70, and moves the light distribution adjustment unit 60 to a desired position in the optical axis direction.

The LD 20 emits the primary light (blue laser light), and the primary light emitted is guided by the optical fiber 40. The optical converter 51 of the optical conversion unit 50 is irradiated with the primary light emitted from the optical fiber emission end 41 (indicated by the solid-line arrow in FIG. 3). The light distribution angle of the primary light emitted from the optical fiber emission end 41 is narrow, and in the present embodiment the primary light has light distribution characteristics of a first light distribution angle (in which a light distribution half-value angle is about 15°).

Of the primary light irradiated to the optical converter 51, light that is not absorbed into the phosphor powder and light diffused by the diffusion particles have diffusion angles different from that of the primary light emitted from the optical fiber emission end 41. In the present embodiment, this light is defined as primary diffused light (indicated by the dashed-line arrow in FIG. 3).

Part of the primary light irradiated to the optical converter 51 is absorbed into the phosphor powder and subjected to wavelength conversion. The wavelength conversion light (fluorescence) (indicated by the dashed-dotted-line arrow in FIG. 3) emits light omnidirectionally inside the optical converter 51.

Furthermore, part of the primary diffused light and the fluorescence is emitted in a direction opposite to the traveling direction of the primary light emitted from the optical fiber emission end 41 in the optical converter 51. The light emitted in the opposite direction is reflected by the first reflector 54 and emitted toward the emission surface 51a. The primary diffused light and the fluorescence are repeatedly diffused by the optical converter 51 and reflected by the first reflector 54, and emitted as secondary light having a wide light distribution from the emission surface 51a. In the present embodiment, a mixed light of the primary diffused light and the fluorescence emitted from the emission surface 51a is defined as secondary light. The optical conversion unit 50 converts the primary light having the first light distribution angle to the secondary light having a second light distribution angle (in which a light distribution half-value angle is about 125°) different from the first light distribution angle, i.e., converts the light distribution characteristics thereof. The secondary light exhibits light distribution characteristics symmetric with respect to the optical axis.

Of the secondary light emitted from the optical conversion unit 50, components near the optical axis (90° direction in FIG. 4) are directly irradiated to the coverglass incident surface 63*a* that is away from the emission surface 51*a* by distance A3. The irradiated light is transmitted through the coverglass 63 and emitted as illumination light.

In the wide light distribution mode, distance A3 between the emission surface 51*a* and the coverglass incident surface 63*a* is small. For only components near the axis orthogonal to the optical axis (0° direction and 180° direction in FIG. 4) out of those of the secondary light, light paths are changed by the second reflector 62 of the light distribution adjustment unit 60 and they are emitted as illumination light. In the present embodiment, the light whose light distribution angle is adjusted from the second light distribution angle of the secondary light by the light distribution adjustment unit 60 is defined as illumination light having a third light distribution angle. In the wide light distribution mode, the light distribution adjustment unit 60 adjusts the secondary light of the second light distribution angle to the illumination light of the third light distribution angle (in which a light distribution half-value angle is 120°) while maintaining the wide light distribution.

In the present embodiment, the adjustment amount when the secondary light of the second light distribution angle is adjusted to illumination light of the third light distribution angle by the light distribution adjustment unit 60 is defined as a light distribution adjustment amount. In the wide light distribution mode, the light distribution adjustment amount when the second light distribution angle of the secondary light is adjusted to the third light distribution angle of the illumination light by the light distribution adjustment unit 60 is a small amount of 5°, and the third light distribution angle of the illumination light exhibits light distribution characteristics close to the characteristics of the second light distribution angle of the secondary light.

(Operation in First Narrow Light Distribution Mode)

Figure 5:
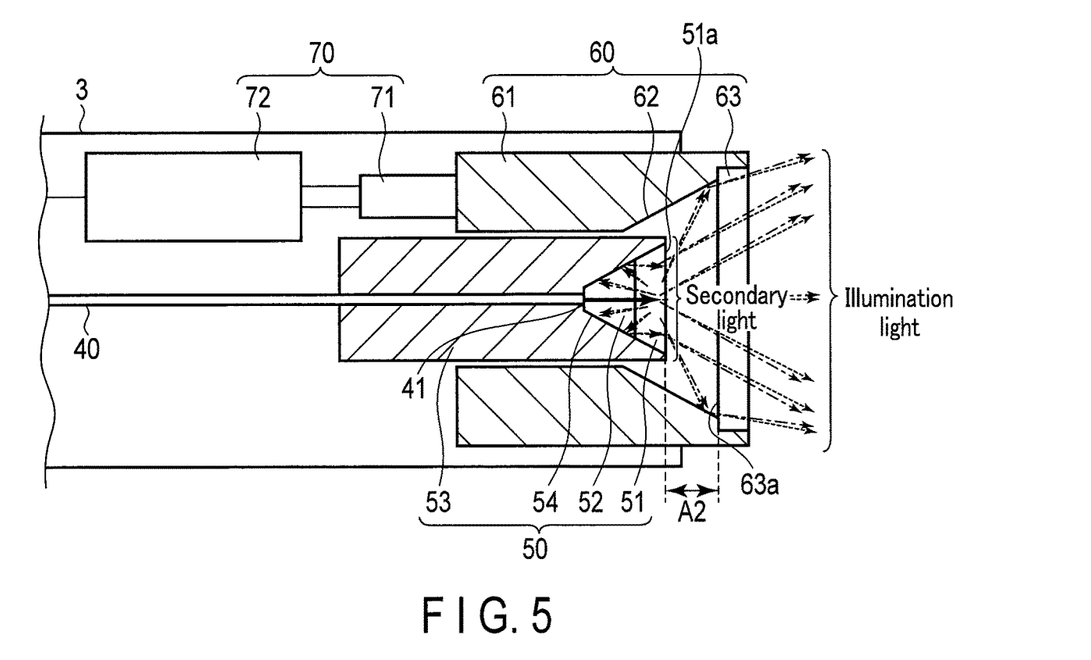
FIG. 5 is a view showing an example of primary light, primary diffused light, and fluorescence when illumination light is emitted from the light source device in a first narrow light distribution mode.
Figure 6:
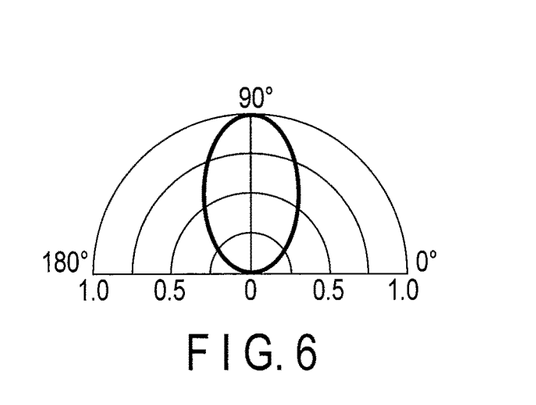
FIG. 6 shows an example of light distribution characteristics of illumination light in the first narrow light distribution mode.

FIG. 5 is a view showing an example of primary light, primary diffused light, and fluorescence when illumination light is emitted from the light source device in a first narrow light distribution mode. FIG. 6 shows an example of light distribution characteristics of illumination light in the first narrow light distribution mode.

The first narrow light distribution mode is a mode in which the light source device 1 emits illumination light having a narrower light distribution (e.g., light distribution half-value angle of 65°) than the wide light distribution mode. When the user selects the first narrow light distribution mode, the device controller 90 reads out, from the light distribution characteristics control information stored in the light distribution angle information storage 80, distance A2 (FIGS. 5 and 9) between the emission surface 51*a* of the optical conversion unit 50 and the coverglass incident surface 63*a* of the light distribution adjustment unit 60. The device controller 90 drives the light distribution adjustment unit driver 70 to move the light distribution adjustment unit 60 in the optical axis direction so that the distance between the emission surface 51*a* and the coverglass incident surface 63*a* becomes A2 (A2>A3). The operation relating to the movement of the light distribution adjustment unit 60 by the device controller 90 is similar to that in the wide light distribution mode, and a description of such operation will be omitted. The operation of the primary light in the optical conversion unit 50 is similar to that in the wide light distribution mode, and a description of such operation will be omitted.

Of the secondary light emitted from the optical conversion unit 50, components near the optical axis (90° direction in FIG. 6) are, in a manner similar to the wide light distribution mode, directly irradiated to the coverglass incident surface 63*a* that is away from the emission surface 51*a* by distance A2, transmitted through the coverglass 63, and emitted as illumination light.

Part of the secondary light other than the components near the optical axis is reflected by the second reflector 62 located further forward (distal side) of the optical conversion unit 50, and the light path thereof is changed, allowing emission as illumination light. Since distance A2 between the emission surface 51*a* and the coverglass incident surface 63*a* is longer than distance A3, the amount of the secondary light irradiated to the second reflector 62 increases. In the first narrow light distribution mode, the secondary light of the second light distribution angle is adjusted to illumination light of the third light distribution angle (in which a light distribution half-value angle is 65°). The light distribution adjustment amount for adjustment from the second light distribution angle of the secondary light to the third light distribution angle of the illumination light is a large amount of 60°, exhibiting the light distribution characteristics in which the third light distribution angle of the illumination light is narrower than the second light distribution angle of the secondary light.

An amount for adjustment from the second light distribution angle of the secondary light to the third light distribution angle of the illumination light by the light distribution adjustment unit 60 is defined as a light distribution adjustment amount. The light distribution adjustment unit 60 light-distribution converts the light distribution half-value angle of the secondary light emitted from the emission surface 51*a* of the optical conversion unit 50 from about 125° to about 65°, and the light distribution convent amount is defined as a light distribution adjustment amount by the light distribution adjustment unit 60. The light distribution adjustment amount, in this case, is about 60°. Thus, the light distribution conversion amount by the optical conversion unit 50 (from 15° to 125°) is greater than the light distribution adjustment amount by the light distribution adjustment unit 60 (from 125° to 65°).

(Operation in Second Narrow Light Distribution Mode)

Figure 7:
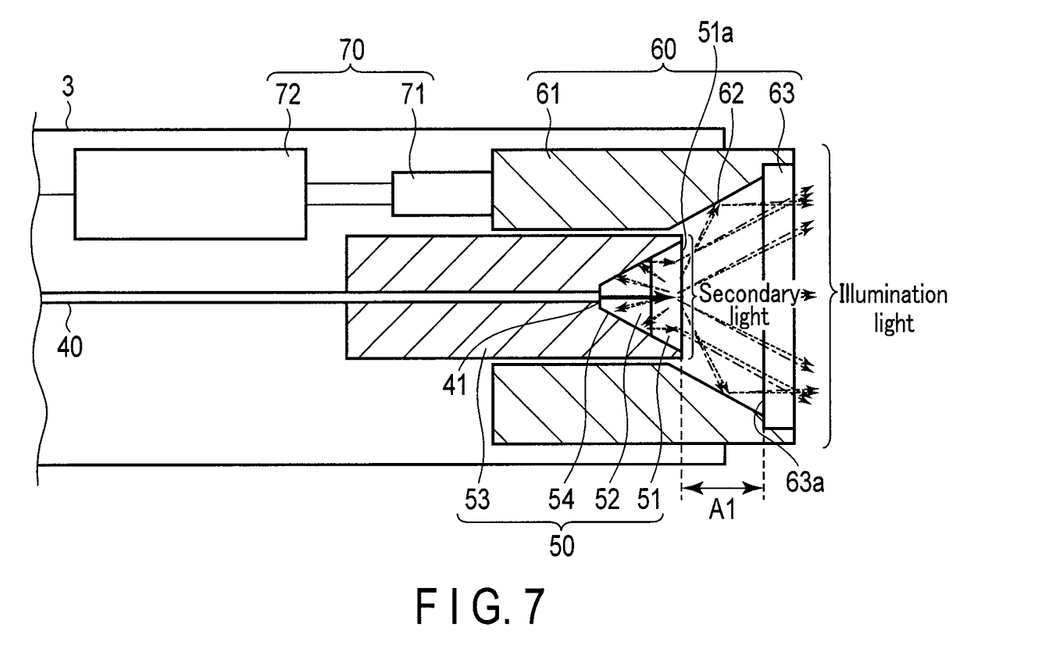
FIG. 7 is a view showing an example of primary light, primary diffused light, and fluorescence when illumination light is emitted from the light source device in a second narrow light distribution mode.
Figure 8:
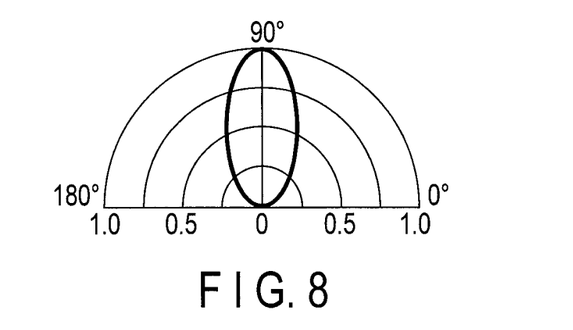
FIG. 8 shows an example of light distribution characteristics of illumination light in the second narrow light distribution mode.

FIG. 7 is a view showing an example of primary light, primary diffused light, and fluorescence when illumination light is emitted from the light source device in a second narrow light distribution mode. FIG. 8 shows an example of light distribution characteristics of illumination light in the second narrow light distribution mode.

The second narrow light distribution mode is a mode in which the light source device 1 emits illumination light having a narrower light distribution (e.g., light distribution half-value angle of 50°) than the first narrow light distribution mode. When the user selects the second narrow light distribution mode, the device controller 90 reads out, from the light distribution characteristics control information stored in the light distribution angle information storage 80, distance A1 (FIG. 7) between the emission surface 51*a* of the optical conversion unit 50 and the coverglass incident surface 63*a* of the light distribution adjustment unit 60. The device controller 90 drives the light distribution adjustment unit driver 70 to move the light distribution adjustment unit 60 in the optical axis direction so that the distance between the emission surface 51a and the coverglass incident surface 63a becomes A1 (A1>A2>A3). The operation relating to the movement of the light distribution adjustment unit 60 by the device controller 90 is similar to that in the other modes, and a description of such operation will be omitted. The operations of the primary and secondary lights in the optical conversion unit 50 are similar to those in the other modes, and a description of such operations will be omitted.

In the second narrow light distribution mode, in a manner similar to the first narrow light distribution mode, part of the secondary light is reflected by the second reflector 62 located further forward (distal side) of the optical conversion unit 50 and the light path thereof is changed, allowing emission as illumination light. Since distance A1 between the emission surface 51a and the coverglass incident surface 63a is longer than distance A2, the amount of the secondary light irradiated to the second reflector 62 increases. In the second narrow light distribution mode, the light distribution adjustment unit 60 light-distribution converts the light distribution half-value angle of the secondary light emitted from the emission surface 51a of the optical conversion unit 50 from about 125° to about 50°, and the light distribution adjustment amount is about 75°.

In the present embodiment, examples of three light distribution characteristics (light distribution angles) at distances A1, A2, and A3 have been described but are not limited thereto, and it is possible to adjust, depending on positions on the optical axis of the light distribution adjustment unit 60, the light distribution characteristics of illumination light within the range of 35° to 120° of the light distribution half-value angle. As described above, the light distribution adjustment amount increases as the distance is longer.

The emission surface 51a of the optical conversion unit 50 is preferably arranged in a region where the second taper surface 61c formed on the second holder 61 of the light distribution adjustment unit 60 is present in the optical direction. That is, the secondary light emitted from the emission surface 51a is reflected by the second taper surface 61c and then transmitted through the coverglass 63, thereby a light transmittance of the coverglass 63 does not change depending on the location of the light distribution adjustment unit 60 (maintaining a high light transmittance).

In a configuration in which the light distribution adjustment unit 60 is provided further forward of the position illustrated in FIG. 7 and the emission surface 51a of the optical conversion unit 50 is located inside the guide hole 61a of the second holder 61, the secondary light is repeatedly reflected in the guide hole 61a, which results in lowering the light acquisition efficiency. Thus, it is not preferable to arrange the light distribution adjustment unit 60 at a position further forward of the position illustrated in FIG. 7.

FIG. 9 is a diagram showing an example of a relationship between the light distribution half-value angle of the illumination light and the distance between the emission surface 51a of the optical conversion unit 50 and the coverglass emission surface 63a of the light distribution adjustment unit 60, i.e., light distribution characteristics control information. It has been found through experiments, etc. that the light distribution half-value angle exhibits characteristics in which the angle does not change linearly according to the distance. To be specific, if the distance is small (less than 0.1 mm), the light distribution half-value angle moderately changes from the wide light distribution angle to the narrow light distribution angle in accordance with the change in the relative position of the coverglass incident surface 63a to the emission surface 51a. When the distance is slightly longer (around 0.1 to 0.2 mm), the light distribution half-value angle rapidly changes to the narrow light distribution angle by the small relative position change. When the distance is longer (0.2 mm or more), the light distribution half-value angle moderately changes in accordance with the change in the relative position, and the narrow light distribution angle is maintained. Thus, the second reflector 62 is required to have a predetermined length to adjust the light distribution angle of the secondary light by the light distribution adjustment unit 60. In the present embodiment, a length in the slope direction of the second reflector 62 on the second taper surface 61c is longer than a length in the slope direction of the first reflector 54 on the first taper surface 53c.

The taper angle of the second reflector 62 may be the same as the taper angle of the first reflector 54, or may be set as appropriate in consideration of the light distribution adjustment range for light-distribution adjusting the secondary light to the illumination light or a mounting space. For example, when the taper angle of the second reflector 62 is 17° which is smaller than the angle of 25° of the present embodiment, the light distribution characteristics corresponding to the change in the relative position tends to moderately change as compared to when the angle is 25°. In addition, when the taper angle is 35° which is larger than 25° of the present embodiment, the light distribution characteristics corresponding to the change in the relative position tends to change rapidly (greatly) as compared to when the angle is 25°.

The light source device 1 in the present embodiment can be mounted on, for example, a medical or an industrial endoscope.

Figure 10:
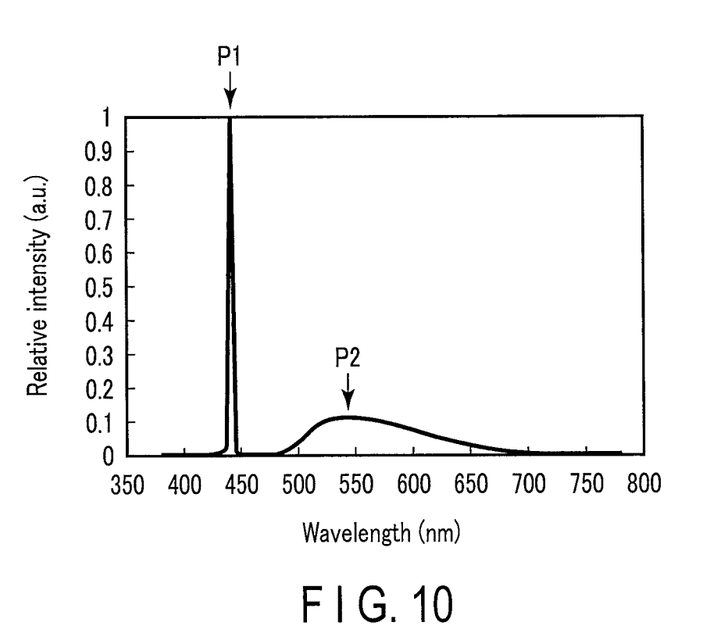
FIG. 10 is a diagram showing illumination spectral characteristics of illumination light.

FIG. 10 is a diagram showing illumination spectral characteristics of illumination light. The illumination light is white light in which the primary diffused light (blue laser light) having peak P1 and yellow fluorescence having peak P2 as shown in FIG. 10 are mixed and the correlated color temperature is about 6000K. The illumination spectrum is determined by conditions of given concentrations and thickness of the phosphor powder and the diffusion particles provided in the optical conversion unit 50. The illumination spectrum of the secondary light emitted from the optical conversion unit 50 is similar to that shown in FIG. 10.

The second reflector 62 formed on the second holder 61 of the light distribution adjustment unit 60 has equivalent reflectivity characteristics in the blue region of the primary diffused light and the yellow region of the fluorescence. The primary diffused light and the fluorescence emitted from the optical conversion unit 50 are emitted with uniform light distribution characteristics. Thus, even if the light distribution characteristics of the illumination light are changed by the light distribution adjustment unit 60, the same emission colors can be maintained.

The surface on which the second reflector 62 is formed on the second holder 61 of the light distribution adjustment unit 60 is not limited to a taper shape, and may be a concave surface of a paraboloidal shape and the like. Furthermore, the surface on which the second reflector 62 is formed may be a truncated-conical shaped taper surface having a different diameter from that of the taper surface of the second holder 61, not the truncated-conical shaped taper surface. The surface on which the first reflector 54 is formed on the first holder 53 of the optical conversion unit 50 is not limited to a taper shape, and may be a cylindrical shape.

The light distribution adjustment unit driver 70 may be a static actuator, a hydraulic actuator, a piezo actuator, a rubber actuator, etc., instead of the micromotor 72 (electromagnetic actuator). The same applies to an optical conversion unit driver 170 in the second embodiment described later. Alternatively, the user may move the light distribution adjustment unit 60 without using the light distribution adjustment unit driver 70, or by manually sliding, for example, without providing the driver.

Advantageous Effects

The present embodiment can provide a light source device 1 capable of adjusting a light distribution adjustment amount by arranging the light distribution adjustment unit 60 slidable with respect to the optical conversion unit 50. Further, the present embodiment can provide a light source device 1 capable of receiving the secondary light emitted from the optical conversion unit 50, capable of adjusting the light distribution adjustment amount in a stepwise or continuous manner beyond the two-stage adjustment by moving the light distribution adjustment unit 60 provided with the second reflector 62 in the optical axis direction, and capable of irradiating illumination light having different light distribution angles depending on the light distribution adjustment amount.

Furthermore, according to the present embodiment, the light source device 1 stores in advance the light distribution characteristics control information indicating the relative distance between the emission surface 51a of the optical converter 51 of the optical conversion unit 50 and the coverglass incident surface 63a of the light distribution adjustment unit 60, and the light distribution characteristics of illumination light (light distribution angle), and based on thereon, the light distribution adjustment unit 60 is moved back and forth to allow emission of illumination light with predetermined light distribution characteristics.

The coverglass 63 is adhered to the emission end side of the second holder 61 of the light distribution adjustment unit 60, and they are moved integrally. Thus, even if a distance between the emission surface 51a and the coverglass incident surface 63a is separated, a reduction in the amount of peripheral light, so-called vignetting, does not likely occur. Accordingly, the high light transmittance of the coverglass 63 can be maintained.

The phosphor and the diffuser that constitute the optical converter 51 of the optical conversion unit 50 and the first reflector 54 allow emission of the secondary light having the uniform light distribution of the primary diffused light and fluorescent components from the optical conversion unit 50.

Second Embodiment

Figure 11:
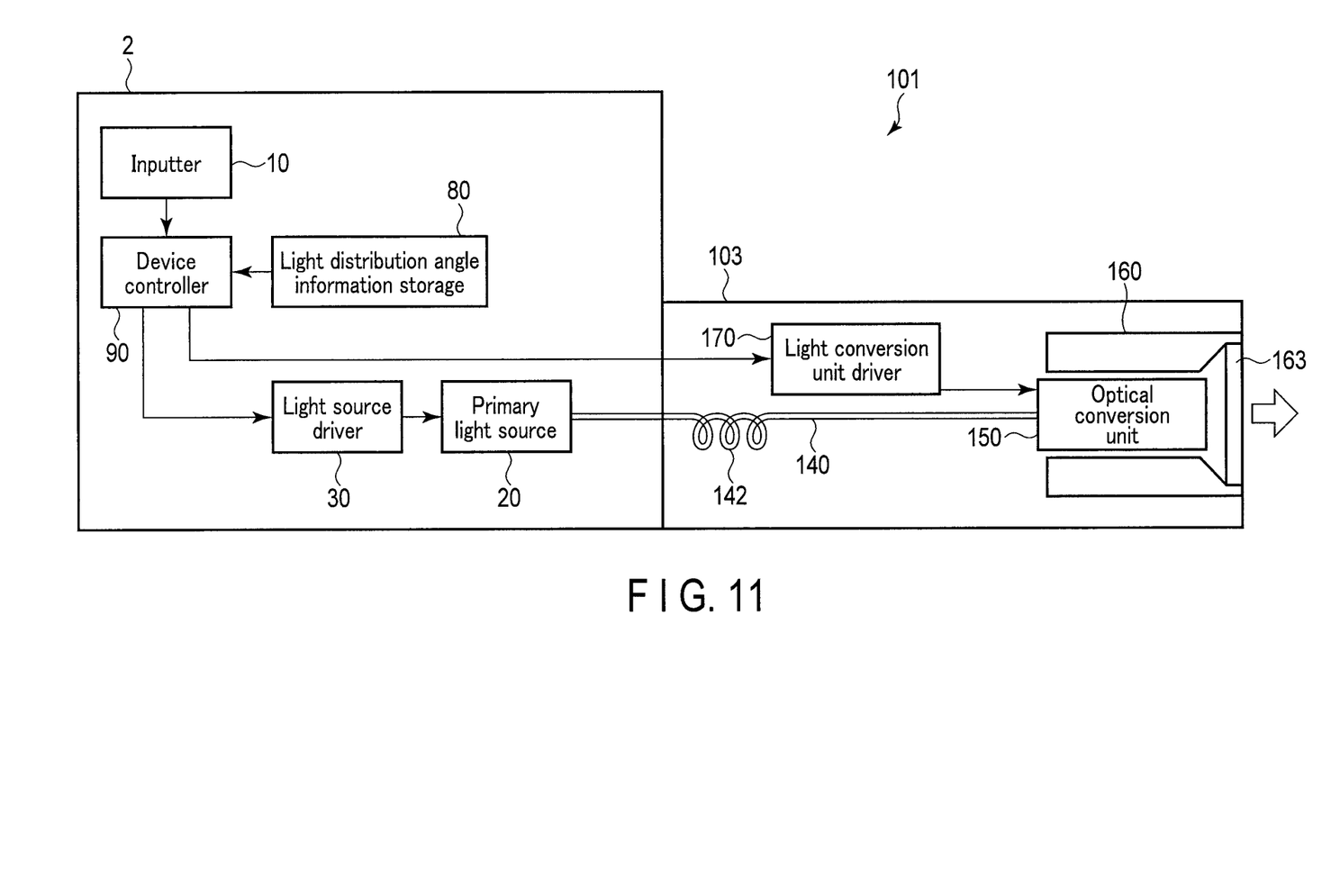
FIG. 11 is a block diagram schematically showing a light source device according to a second embodiment.
Figure 12:
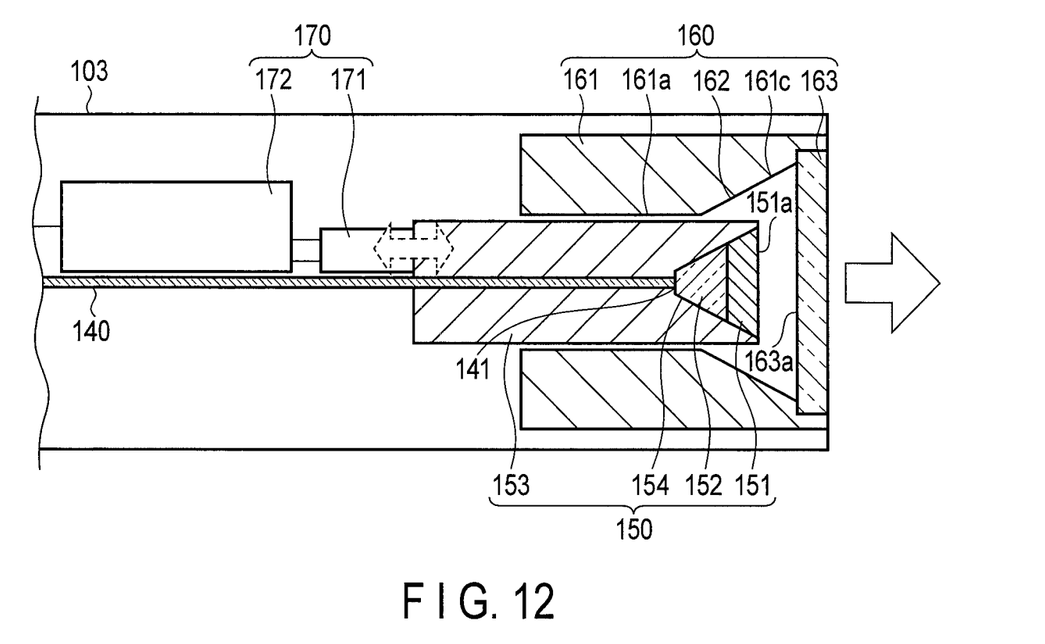
FIG. 12 is a view schematically showing a distal end of the light source device according to the second embodiment.

A light source device 101 of the second embodiment of the present invention will be explained with reference to FIG. 11 and FIG. 12. In the following explanation, the same reference symbols as used in the first embodiment will be used for the same parts, and detailed explanations thereof will be omitted, and only parts different from the first embodiment will be explained.

(Configuration)

In the present embodiment, a light distribution adjustment unit 150 is coupled to an optical conversion unit driver 170, and is configured to be movable in the optical axis direction of the primary light emitted from the optical fiber emission end 41a. The optical conversion unit 150 includes an optical converter 151, a transparent member 152, a first holder 153, and a first reflector 154. They have structures similar to the corresponding structural elements in the first embodiment unless otherwise explicitly noted.

The optical conversion unit 160 is arranged near the distal end of the insertion section 3 and fixed inside the insertion section 3 by an adhesive member and the like. The light distribution adjustment unit 160 includes a second holder 161, a second reflector 162, and a coverglass 163. They have structures similar to the corresponding structural elements in the first embodiment unless otherwise explicitly noted. In the present embodiment, the coverglass 163 is adhered and fixed to the second holder 161 to be integrated, but they may be separate.

The optical conversion unit driver 170 has a function of moving (advancing and retreating) the optical conversion unit 150 backward and forward on the optical axis of the primary light emitted from the optical fiber emission end 141. Upon receipt of the driving signal from the device controller 90, the optical conversion unit driver 170 is driven to slide the optical conversion unit 150 on the optical axis of the primary light. The optical conversion unit driver 170 includes a ball screw 171 which, for example, is a holder, and a micromotor 172 coupled to the ball screw 171. The ball screw 171 is screwed to the screw hole (not shown) formed on the first holder 153 of the optical conversion unit 150. When the ball screw 171 is rotationally driven in one direction by the micromotor 172, the optical conversion unit 150 moves in the traveling direction on the optical axis with respect to the light distribution adjustment unit 160, and when the ball screw 171 is rotationally driven in the other direction, the optical conversion unit 150 moves in a direction opposite to the traveling direction on the optical axis.

In the present embodiment, the optical conversion unit 150 is arranged to be slidable with respect to the light distribution adjustment unit 160 by the optical conversion unit driver 170.

An optical fiber 140 in the present embodiment has an expansion/contraction property and flexibility. Thus, the optical fiber 140 can be expanded and contracted in accordance with the back-and-forth movement of the optical conversion unit 150 on the optical axis. The optical fiber 140 includes an optical fiber surplus 142 located between the LD 20 and the optical conversion unit 150 and having a length longer than the movable distance of the optical conversion unit 150. The optical fiber surplus 142 is, for example, a portion where part of the optical fiber 140 is wound spirally and is arranged in the insertion section 3.

(Operation)

The user enters into an inputter 10 a mode selected from three operation modes of the light source device 1 (a wide light distribution mode, a first narrow light distribution mode, and a second narrow light distribution mode). Information on the entered mode is transmitted from the inputter 10 to the device controller 90. The device controller 90 reads out the light distribution characteristics control information corresponding to the selected mode from the light distribution angle information storage 80 and controls the optical conversion unit driver 170 to change the relative position of the optical conversion unit 150 with respect to the optical conversion unit 160. For example, the device controller 90 controls the position of the optical conversion unit 150 relative to the light distribution adjustment unit 160 in a stepwise manner by the optical conversion unit driver 170. The illumination light emitted from the light source device 1 in each mode is similar to that in the first embodiment.

For example, when the user selects the wide light distribution mode, the device controller 90 reads out, from the light distribution characteristics control information stored in the light distribution angle information storage 80, distance A3 corresponding to this light distribution angle between the emission surface 151a of the optical conversion unit 150 and the coverglass incident surface 163a of the light distribution adjustment unit 160. The device controller 90 drives the optical conversion unit driver 170 to move the light distribution adjustment unit 150 in the optical axis direction so that the distance between the emission surface 151a and the coverglass incident surface 163a becomes A3. In a similar manner, when the user selects the first narrow light distribution mode and the second narrow light distribution mode, the device controller 90 drives the optical conversion unit driver 170 to move the optical conversion unit 150 in the optical axis direction to obtain distance A2 and A1.

In order to efficiently emit the secondary light as illumination light, the preferable range in which the optical conversion unit 150 is moved on the optical axis is a range from an emission end of the light distribution adjustment unit 160 to a position where the second taper surface 161c of the light distribution adjustment unit 160 is present (a degree of thickness of the coverglass 163).

Advantageous Effects

The present embodiment can provide the light source device 1 capable of adjusting light distribution characteristics of illumination light by combining the optical conversion unit 150 movable in the optical axis direction and the optical fiber 40 comprising the optical fiber surplus 142 movable according to the movement of the optical conversion unit 150, without changing the shape of the end of the insertion section 3.

Variant of Second Embodiment

In the variant, the optical converter 151 of the optical conversion unit 150 does not contain a phosphor, and only a diffuser for diffusing the primary light is sealed by the silicon resin. In this optical converter 151, heat generation due to conversion loss by wavelength conversion does not occur.

With such a configuration, the primary diffused light is only emitted as the secondary light emitted from the optical conversion unit 150, and a light distribution angle of the primary diffused light changes depending on the position of the light distribution adjustment unit 160.

According to the variant, heat generation due to loss at the light converting time of the optical conversion unit 150 is reduced more than in the second embodiment, and the light distribution characteristics of the secondary light can be adjusted as illumination light without changing the shape of the end of the insertion section 3 of the light source device 1.

The embodiments of the present invention have been described as in the foregoing; however, the present invention is not limited thereto, and various improvements and changes can be made without departing from the gist of the present invention. For example, the primary light is not limited to blue laser light, and a light distribution mode to be set is not limited to the wide light distribution mode, the first narrow light distribution mode, the second narrow light distribution mode, etc.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
   a primary light source that emits primary light;
   a light guide that guides the primary light;
   an optical conversion material that converts the primary light emitted from the light guide and having a first light distribution angle into secondary light having a second light distribution angle different from the first light distribution angle and emits the secondary light;
   a light distribution adjustment material that adjusts the secondary light having the second light distribution angle to illumination light having a third light distribution angle and emits the illumination light, wherein one of the light distribution adjustment material and the optical conversion material is arranged to be movable relative to the other, the light distribution adjustment material being configured to adjust a light distribution adjustment amount that is an amount for adjusting the second light distribution angle of the secondary light to the third light distribution angle of the illumination light;
   a controller configured to move the optical conversion material along the optical axis of the primary light emitted from the light guide, wherein on the optical axis of the primary light, the light distribution adjustment amount increases as a distance between a secondary light emission end of the optical conversion material moved by the controller and a secondary light incident end of the light distribution adjustment material increases; and
   a light distribution angle information memory that stores light distribution angle control information indicating a relationship between the distance between the secondary light emission end of the optical conversion material and the secondary light incident end of the light distribution adjustment material, and light distribution characteristics of the illumination light;
   wherein the controller moves the optical conversion material based on the light distribution angle control information read out from the light distribution angle information memory.

2. The light source device according to claim 1, further comprising a reflector that receives the secondary light and changes a traveling direction of the secondary light,
   the reflector being arranged at a portion excluding a region on an optical axis of the primary light emitted from the light guide.

3. The light source device according to claim 1, further comprising a cover glass that transmits the secondary light,
   the cover glass being arranged at a region on the optical axis of the primary light and being fixed to an emission end side of the light distribution adjustment material.

4. The light source device according to claim 1, wherein the third light distribution angle is smaller than the second light distribution angle.

5. The light source device according to claim 1, wherein a light distribution adjustment amount of the primary light representing an amount for converting the light distribution angle of the primary light to the light distribution angle of the secondary light by the optical conversion material is greater than a light distribution adjustment amount of the secondary light.

6. A light source device comprising:
   a primary light source that emits primary light;

a light guide that guides the primary light;
an optical conversion material that converts the primary light emitted from the light guide and having a first light distribution angle into secondary light having a second light distribution angle different from the first light distribution angle and emits the secondary light;
a light distribution adjustment material that adjusts the secondary light having the second light distribution angle to illumination light having a third light distribution angle and emits the illumination light, wherein one of the light distribution adjustment material and the optical conversion material is arranged to be movable relative to the other, the light distribution adjustment material being configured to adjust a light distribution adjustment amount that is an amount for adjusting the second light distribution angle of the secondary light to the third light distribution angle of the illumination light; and
a controller configured to move the optical conversion material along the optical axis of the primary light emitted from the light guide, wherein on the optical axis of the primary light, the light distribution adjustment amount increases as a distance between a secondary light emission end of the optical conversion material moved by the controller and a secondary light incident end of the light distribution adjustment material increases;
wherein the optical conversion material receives and converts the primary light into primary diffused light and emits at least part of the primary diffused light backward with respect to a traveling direction of the optical axis of the primary light;
the light source device further comprising:
a first reflector that receives the primary diffused light and reflects at least part of the received primary diffused light forward with respect to a traveling direction of the optical axis of the primary light;
a first holder that holds the optical conversion material,
a second holder having a through hole larger than an outer diameter of the first holder, and
the light distribution adjustment material comprises a second reflector that receives the secondary light and changes a traveling direction of the secondary light, the second reflector being arranged at a portion excluding a region on an optical axis of the primary light emitted from the light guide, the second reflector being arranged at at least part of the through hole; and
the controller moves the optical conversion material to move the first holder in the through hole.

7. The light source device according to claim 6, wherein the optical conversion material is a material that absorbs and converts part of the primary light into wavelength conversion light having a wavelength region different from that of the primary light, or a complex of the material and a diffuser that diffuses a light distribution angle of the primary light, and
the secondary light is a mixed light obtained by mixing the primary diffused light and the wavelength conversion light, and light distribution angles of the primary diffused light emitted from the optical conversion material and the wavelength conversion light are approximately equal.

8. The light source device according to claim 7, wherein a light distribution adjustment amount of the primary diffused light and a light distribution adjustment amount of the wavelength conversion light by the light distribution adjustment material are approximately equal.

9. The light source device according to claim 6, wherein a second length of the second reflector on the optical axis of the primary light is longer than a first length of the first reflector on the optical axis of the primary light.

10. A light source device comprising:
a primary light source that emits primary light;
a light guide that guides the primary light;
an optical conversion material that converts the primary light emitted from the light guide and having a first light distribution angle into secondary light having a second light distribution angle different from the first light distribution angle and emits the secondary light;
a light distribution adjustment material that adjusts the secondary light having the second light distribution angle to illumination light having a third light distribution angle and emits the illumination light, wherein one of the light distribution adjustment material and the optical conversion material is arranged to be movable relative to the other, the light distribution adjustment material being configured to adjust a light distribution adjustment amount that is an amount for adjusting the second light distribution angle of the secondary light to the third light distribution angle of the illumination light;
the light distribution adjustment material comprises a reflector that receives the secondary light and changes a traveling direction of the secondary light, the reflector being arranged at a portion excluding a region on an optical axis of the primary light emitted from the light guide;
a controller configured to move the light distribution adjustment material along the optical axis of the primary light emitted from the light guide, wherein on the optical axis of the primary light, the light distribution adjustment amount increases as a distance between a secondary light emission end of the optical conversion material and a secondary light incident end of the light distribution adjustment material moved by the controller increases; and
a light distribution angle information memory that stores light distribution angle control information indicating a relationship between the distance between the secondary light emission end of the optical conversion material and the secondary light incident end of the light distribution adjustment material, and light distribution characteristics of the illumination light;
wherein the controller moves the light distribution adjustment material based on the light distribution angle control information read out from the light distribution angle information memory.

11. The light source device according to claim 10, wherein the optical conversion material receives and converts the primary light into primary diffused light having a light distribution angle wider than the first light distribution angle of the primary light, and emits at least part of the primary diffused light backward with respect to a traveling direction of the optical axis of the primary light;
a first reflector that receives and reflects the primary diffused light;
a first holder that holds the optical conversion material, and
a second holder having a through hole larger than an outer diameter of the first holder, the reflector being a second reflector, the second reflector being arranged at at least part of the through hole, wherein the controller moves the light distribution adjustment material along an outer periphery of the first holder.

12. The light source device according to claim 11, wherein at least part of the through hole of the second holder comprises a concave surface that is open to expand toward the traveling direction of the optical axis, and
an emission end of the optical conversion material is arranged at a region where the concave surface exists.

13. The light source device according to claim 10, wherein the controller is further configured to drive the primary light source, and
during a drive control period when the primary light source is driven by the controller, the controller moves the light distribution adjustment material in a direction of the optical axis.

* * * * *